(12) United States Patent (10) Patent No.: US 7,796,260 B1
Johs et al. (45) Date of Patent: Sep. 14, 2010

(54) SYSTEM AND METHOD OF CONTROLLING INTENSITY OF AN ELECTROMAGNETIC BEAM

(75) Inventors: Blaine D. Johs, Lincoln, NE (US); Christopher A. Goeden, Lincoln, NE (US); Galen L. Pfeiffer, Lincoln, NE (US)

(73) Assignee: J.A. Woollam Co., Inc., Lincoln, NE (US)

( * ) Notice: Subject to any disclaimer, the term of this patent is extended or adjusted under 35 U.S.C. 154(b) by 795 days.

(21) Appl. No.: 11/788,796

(22) Filed: Apr. 21, 2007

Related U.S. Application Data

(60) Provisional application No. 60/794,583, filed on Apr. 25, 2006.

(51) Int. Cl.
 *G01J 4/00* (2006.01)
(52) U.S. Cl. ...................................................... 356/369
(58) Field of Classification Search ....................... None
 See application file for complete search history.

(56) References Cited

U.S. PATENT DOCUMENTS

| | | | | | |
|---|---|---|---|---|---|
| 3,782,823 | A | * | 1/1974 | Kantorski et al. | 356/318 |
| 3,905,675 | A | * | 9/1975 | McCracken | 359/434 |
| 4,672,196 | A | * | 6/1987 | Canino | 356/369 |
| 5,206,701 | A | | 4/1993 | Taylor | 356/325 |
| 5,223,715 | A | | 6/1993 | Taylor | 250/343 |
| 5,784,158 | A | * | 7/1998 | Stanco et al. | 356/326 |
| 6,073,464 | A | * | 6/2000 | Boher et al. | 356/369 |
| 6,081,322 | A | * | 6/2000 | Barbour | 356/73.1 |
| 6,134,012 | A | * | 10/2000 | Aspnes et al. | 356/369 |
| 6,169,624 | B1 | * | 1/2001 | Godil et al. | 359/237 |
| 7,099,006 | B1 | | 8/2006 | Johs et al. | 356/369 |

\* cited by examiner

*Primary Examiner*—L. G. Lauchman
*Assistant Examiner*—Juan D Valentin
(74) *Attorney, Agent, or Firm*—James D. Welch (57) ABSTRACT

A system and method of substantially achromatically controlling the intensity of a spectroscopic beam with application in spectrophotometers, reflectometers, ellipsometers, polarimeters or the like systems.

10 Claims, 7 Drawing Sheets

SYSTEM AND METHOD OF CONTROLLING INTENSITY OF AN ELECTROMAGNETIC BEAM

This Application Claims benefit of Provisional Application Ser. No. 60/794,583 Filed Apr. 25, 2006.

TECHNICAL FIELD

The present invention relates to the control of properties of electromagnetic beams, and more particularly to a system and method of substantially achromatically controlling the intensity of a spectroscopic beam.

BACKGROUND

Sources of beams of electromagnetic radiation generally provide intensity vs. wavelength plots which vary with wavelength. In some situations the intensity at one or more wavelengths can be greater than desired as it causes saturation of detector electronics. It is also noted that plots of intensity vs. wavelength have an identifiable "median value". Where intensity is greater than desired at least one wavelength it can be beneficial to uniformly attenuate said median value over the entire wavelength range in an achromatic manner. That is the attenuation of intensity should be substantially the same at each wavelength. Substantially achromatic intensity attenuation systems are known, such as neutral density filters, but they tend to be expensive. Systems are known which beneficially provide non-achromatic attenuation of beam intensity, such as described in U.S. Pat. No. 7,099,006 to Johs et al. Said 006 Patent teaches that reflecting a beam of electromagnetic radiation off a Silicon substrate which has a layer of SiO2 on the reflective surface thereof attenuates the intensity of visible wavelengths more that UV and IR wavelengths.

A computer Search for Patents describing achromatic attenuation of electromagnetic beam intensity applied in ellipsometers or spectrophotometers provided no Patents. However some Patents which discuss achromatic attenuation of beams were identified and are:

Patent No. 6,169,624 to Godil et al.;
Patent No. 5,223,715 to Taylor; and
Patent No. 5,206,701 to Taylor.

A need exists for a system that is relatively inexpensive but that provides substantially achromatic intensity attenuation over a range of wavelengths.

DISCLOSURE OF THE INVENTION

The present invention comprises a system that allows sequentially placing different regions of an essentially achromatic attenuation system in the path of a beam of electromagnetic radiation. In the preferred embodiment said different regions of the attenuation system are distinguished from one another by being comprised of different densities of quasi-uniformly distributed small holes. It is noted that the terminology "quasi-uniformly" means that center to center distances between holes are substantially uniform in a region. For insight, it is noted that each region can, but need not be on the order of ¾ inch in diameter, and each hole can, but need not be on the order of 1/32 inch in diameter and be present in different regions at different densities. Further, each hole can, but need not be of a tapered, (eg. conical where the hole shape is circular as viewed form the front thereof), shape as viewed from the side in cross-section, with the larger diameter being, preferably but not exclusively, on the side thereof through which a beam exits.

The present invention then can comprise a circular disc-shaped wheel with the regions thereof sequentially positioned circumferentially, said regions being distinguished from one another by being comprised of different densities of quasi-uniformly distributed small holes or densities of electromagnetic radiation absorbing material(s). The regions can be merged into one another by a gradual change of the density of small holes or densities of electromagnetic radiation absorbing material(s) and this can be effected by a gradual change of the density of small holes or densities of electromagnetic radiation absorbing material(s).

The present invention system can further comprise a collimating lens positioned to receive a divergent beam provided by an effectively "point" source of electromagnetic radiation, and direct it toward a region of said means for sequentially placing different regions of a system in the path of a beam. In a preferred embodiment said collimated beam is also redirected by a reflecting means, which optionally can serve to selectively attenuate the intensity of some wavelengths more than others, (eg. a silicon wafer with silicon dioxide on its surface), prior to the beam passing through a region of the attenuation system.

Further, said collimating lens is generally positioned at a focal length thereof from said "point" source of the beam. Said focal length, however, can vary with wavelength, and selection of a focal length can serve to emphasize the intensity of the associated wavelength prior to said beam being passed through a region of the present invention attenuation system means for sequentially placing said different regions in the path of a beam.

The present invention system can further comprise a focusing lens which collects the beam after it passes through a region of the attenuation system and focuses it onto, for instance, the end of a fiber optics. It is also noted that the position of the focusing lens with respect to the fiber optic can be selected to emphasize intensity at a desired wavelength, because, as in the case of the collimating lens, the focal length of said focusing lens varies a bit with wavelength.

Again, for emphasis, a present invention circular disc-shaped wheel can have regions thereof sequentially positioned circumferentially, can provide that said regions are distinguished from one another by being comprised of different densities of quasi-uniformly distributed small holes or being comprised of different densities of electromagnetic radiation attenuating material(s). Further, said circular disc-shaped wheel can have the regions merged into one another by a gradual change of the density of small holes or a gradual increase in the density of electromagnetic radiation attenuating material(s).

It is noted that where circular disc-shaped wheel, or optionally a linear element, has small holes in a region thereof, said holes can be of any functional shape, such as shape selected from the group consisting of:

round;
square;
rectangular; and
triangular;

as viewed from the front and of a shape selected from the group:

uniform; and
tapered;

as viewed in side cross-section.

A very general method of adjusting the intensity of a beam of electromagnetic radiation comprises the steps of:

a) providing a substantially collimated beam of electromagnetic radiation;

b) causing a means for sequentially placing different regions of an attenuation system in the path of said beam of electromagnetic radiation to position a desired region thereof in the path of said beam.

As a primary use of the present invention is in an Ellipsometer and Polarimeter System, it is noted that said systems generally comprise:

a Polarization State Generator which comprises a Source of Electromagnetic Radiation which provides a beam, a Polarizer and Optional Compensator prior to a Sample, and after said sample a Reflection or Transmission beam Polarization State Detector which comprises an Analyzer, Optional Compensator and a detector.

Said Source of Electromagnetic Radiation which provides a beam typically comprises:

an essentially "point" source of a beam of electromagnetic radiation;
a collimating lens;
a reflecting means);

prior to a means for sequentially placing different regions of an attenuation system in the path of a beam of electromagnetic radiation.

After said means for sequentially placing different regions of an attenuation system in the path of a beam of electromagnetic radiation are present:

a focusing lens; and
a fiber optic;

from which said fiber optic, an electromagnetic beam enters said detector.

A method of providing a desired amount of intensity attenuation to a beam of electromagnetic radiation comprising the steps of:

a) providing a system for substantially achromatically attenuating the intensity of a beam of electromagnetic radiation comprising:
  an essentially "point" source of a beam of electromagnetic radiation;
  a collimating lens;
  a reflecting means;
  a means for sequentially placing different regions of an attenuation system in the path of a beam of electromagnetic radiation;
  a focusing lens; and
  a fiber optic;

such that in use a beam of electromagnetic radiation is provided by the "point" source thereof, is collimated by collimating lens, redirected by reflecting means, passes through a region of the attenuation system, passes through the focusing lens and enters the end of a fiber optic;

b) causing said essentially "point" source of a beam of electromagnetic radiation to provide a beam of electromagnetic radiation;
c) causing said means for sequentially placing different regions of an attenuation system in the path of said beam of electromagnetic radiation to position a desired region thereof in the path of said beam.

A method of adjusting the intensity of a beam of electromagnetic radiation comprising the steps of:

a) providing an Ellipsometer and Polarimeter System generally comprising:
  a Polarization State Generator which comprises a Source of Electromagnetic Radiation which provides a beam, a Polarizer and Optional Compensator prior to a Sample, and
  after said sample a Reflection or Transmission beam Polarization State Detector which comprises an Analyzer, Optional Compensator and a detector;
  wherein said Source of Electromagnetic Radiation which provides a beam comprises:
    an essentially "point" source of a beam of electromagnetic radiation;
    a collimating lens;
    a reflecting means;
    a means for sequentially placing different regions of an attenuation system in the path of a beam of electromagnetic radiation;
    a focusing lens; and
    a fiber optic;

from which said fiber optic, electromagnetic beam emerges;

b) monitoring the output of the detector of the ellipsometer or polarimeter system while sequentially placing different regions of the attenuation system in the path of a beam of electromagnetic radiation.

The present invention can also be a Spectrophotometer or Reflectometer or the like comprising a source of a beam of electromagnetic radiation, a sample and a detector of electromagnetic radiation after interaction with said sample, comprising as the source of said beam:

a system for substantially achromatically attenuating the intensity of a beam of electromagnetic radiation comprising:
  an essentially "point" source of a beam of electromagnetic radiation;
  a collimating lens;
  a reflecting means;
  a means for sequentially placing different regions of an attenuation system in the path of a beam of electromagnetic radiation;
  a focusing lens; and
  a fiber optic;

such that in use a beam of electromagnetic radiation is provided by the "point" source thereof, is collimated by collimating lens, redirected by reflecting means, passes through a region of the attenuation system, passes through the focusing lens and enters the end of a fiber optic which directs electromagnetic radiation to said detector.

A method of adjusting the intensity of a beam of electromagnetic radiation comprising the steps of:

a) providing a Spectrophotometer or Reflectometer or the like comprising a source of a beam of electromagnetic radiation, a sample and a detector of electromagnetic radiation after interaction with said sample, comprising as the source of said beam:
  a system for substantially achromatically attenuating the intensity of a beam of electromagnetic radiation comprising:
    an essentially "point" source of a beam of electromagnetic radiation;
    a collimating lens;
    a reflecting means;
    a means for sequentially placing different regions of an attenuation system in the path of a beam of electromagnetic radiation;
    a focusing lens; and
    a fiber optic;

such that in use a beam of electromagnetic radiation is provided by the "point" source thereof, is collimated by collimating lens, redirected by reflecting means, passes through a region of the attenuation system, passes through the focusing fens and enters the end of a fiber optic;

b) monitoring the output of the detector of the spectrophotometer or reflectometer or the like system while sequentially placing different regions of the attenuation system in the path of a beam of electromagnetic radiation.

It is to be understood that use of the present invention system can include at least one selection from the group consisting of:

storing at least some data provided by a detector in machine readable media;

analyzing at least some of the data provided by a detector and storing at least some of the results of said analysis in machine readable media;

displaying at least some data provided by a detector by electronic and/or non-electronic means;

analyzing at least some of the data provided by a detector and displaying at least some of the results of said analysis by electronic and/or non-electronic means;

causing at least some data provided by said a detector to produce a signal which is applied to provide a concrete and tangible result;

analyzing at least some of the data provided by a detector and causing at least some thereof to produce a signal which is applied to provide a concrete and tangible result.

The invention will be better understood by reference to the Detailed Description Section of this Specification, in conjunction with the Drawings.

DETAILED DESCRIPTION

Figure 1A:
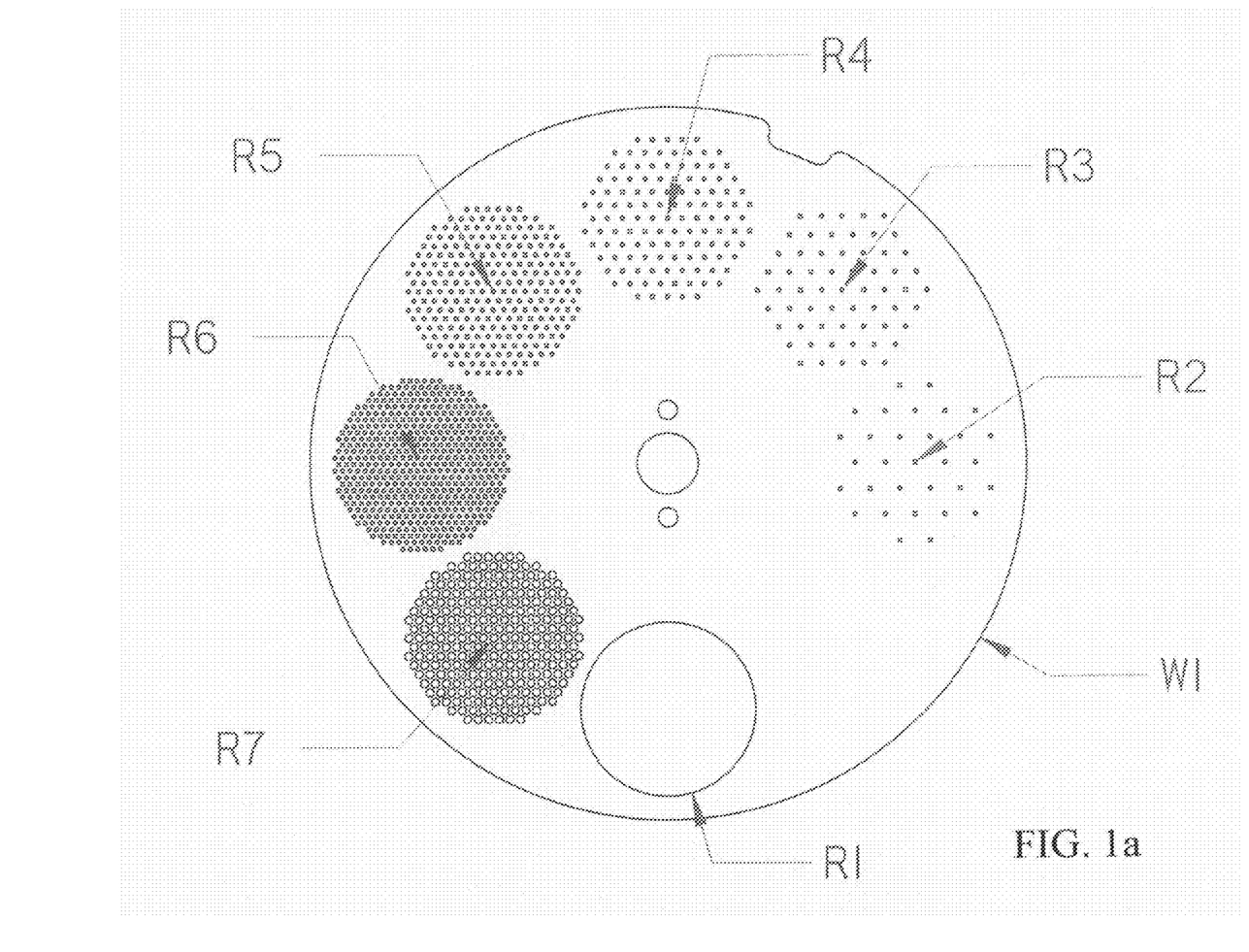
FIG. 1a shows a general front elevational view of a "wheel" means for sequentially placing different regions of an attenuation system (AS) in the path of a beam of electromagnetic radiation.

Turning now to FIG. 1a, there is shown a general front elevational view of a Wheel (W) means for sequentially placing different regions, (eg. (R1) (R2) (R3) (R4) (R5) (R6) (R7), of an attenuation system (AS) in the path of a beam of electromagnetic radiation, in the form of a Wheel of the present invention. It is noted that preferred, non-limiting, examples of Region defining parameters are:

R1 Open;
R2 1.56% open;
R3 3.13% open;
R4 6.25% open;
R5 12.5% open;
R6 25% open;
R7 50% open;

all having preferred 0.020 coned holes and 60 degree pattern.

Figure 1B:
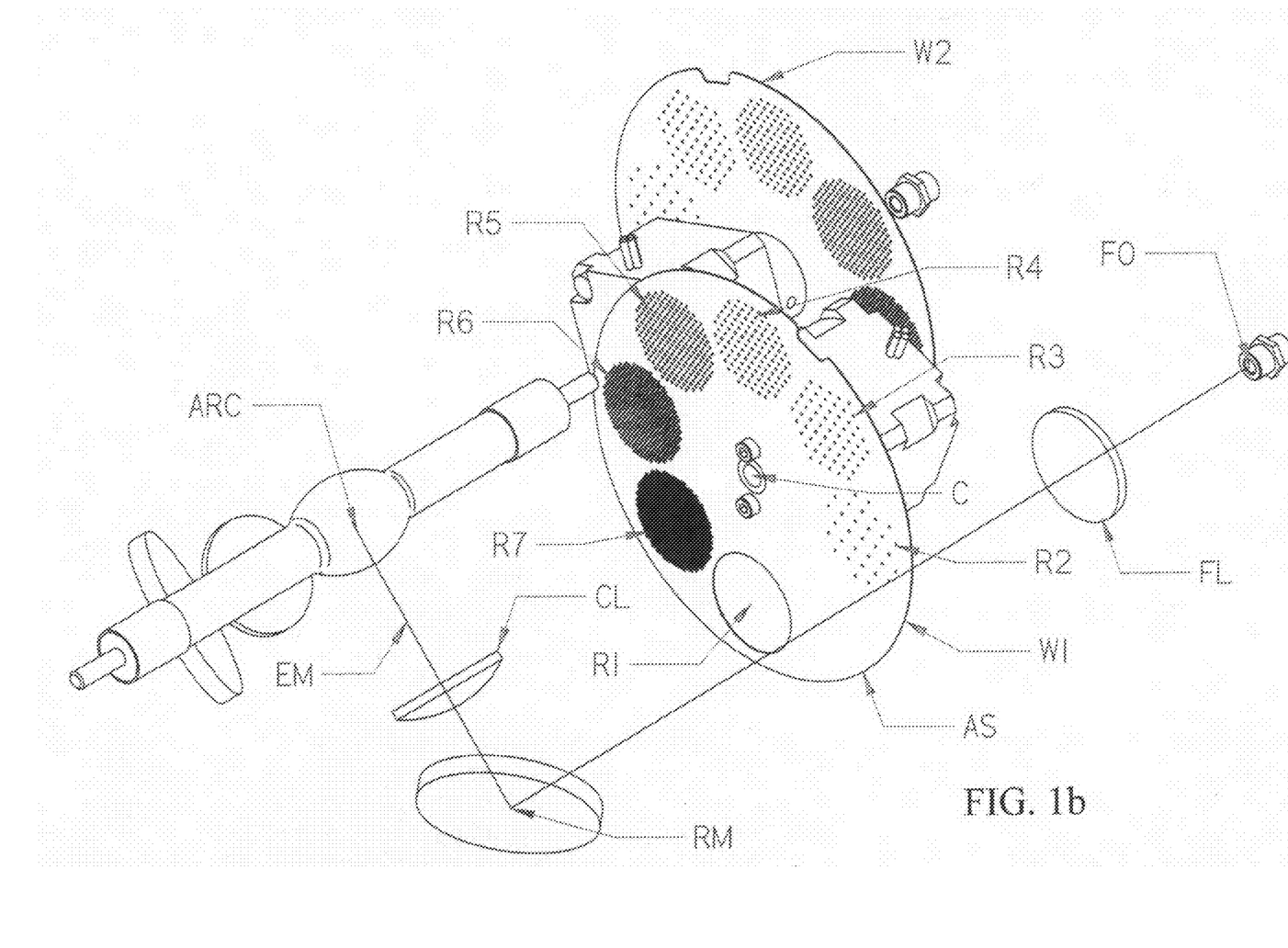
FIG. 1b shows the "wheel" means in FIG. 1a in a system for investigating a sample.

Turning now to FIG. 1b, there is shown:
an arc lamp (ARC) "point" source of a beam (EM) of electromagnetic radiation;
a collimating lens (CL);
a reflecting means (RM);
a means for sequentially placing different regions of an attenuation system (AS) in the path of a beam of electromagnetic radiation;
a focusing lens (FL); and
a fiber optic (FO).

In use a beam (EM) of electromagnetic radiation is provided by the arc lamp (ARC) "point" source thereof, is collimated by collimating lens (CL), redirected by reflecting means (RM), passes through a region of the attenuation system (AS), passes through the focusing lens (FL) and enters the end of a fiber optic (FO).

It is noted that FIGS. 1a and 1b shows the attenuation system (AS) as being comprised of a circular wheel (W1) (W2) with the regions of (W1), (ie. (R1), (R2), (R3), (R6) and (R7) as examples), thereof sequentially positioned circumferentially thereabout such that they are placed in the beam by a rotation motion about the center (C) of said wheel (W1). Another version, (not shown), provides that the regions be linearly offset from one another and that they be slid into the beam. It is noted that the output of the fiber optic (FO) can be the source of an electromagnetic beam in a Reflectometer or Spectrophotometer system which comprises said source, a sample and a detector of electromagnetic radiation after it interacts reflectively or transmissively with said sample. It is also noted that the holes can be of a tapered shape as viewed in side cross-section, with the larger diameter typically oriented on the output side, (ie. the side on which a beam exits therefrom).

Figure 2A:
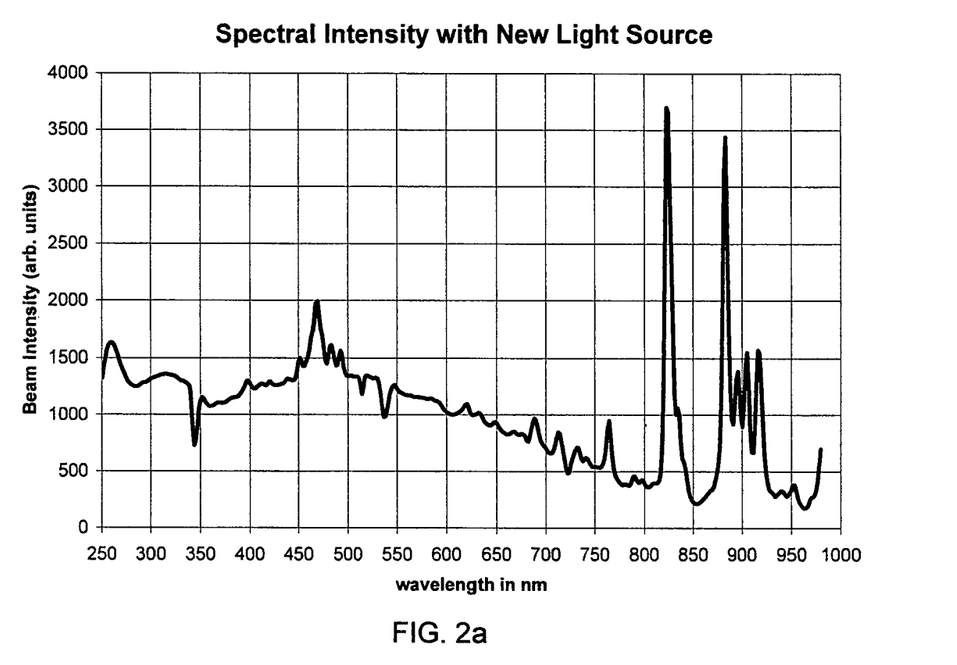
FIG. 2a shows a typical intensity vs. wavelength plot of a source of electromagnetic radiation.
Figure 2B:
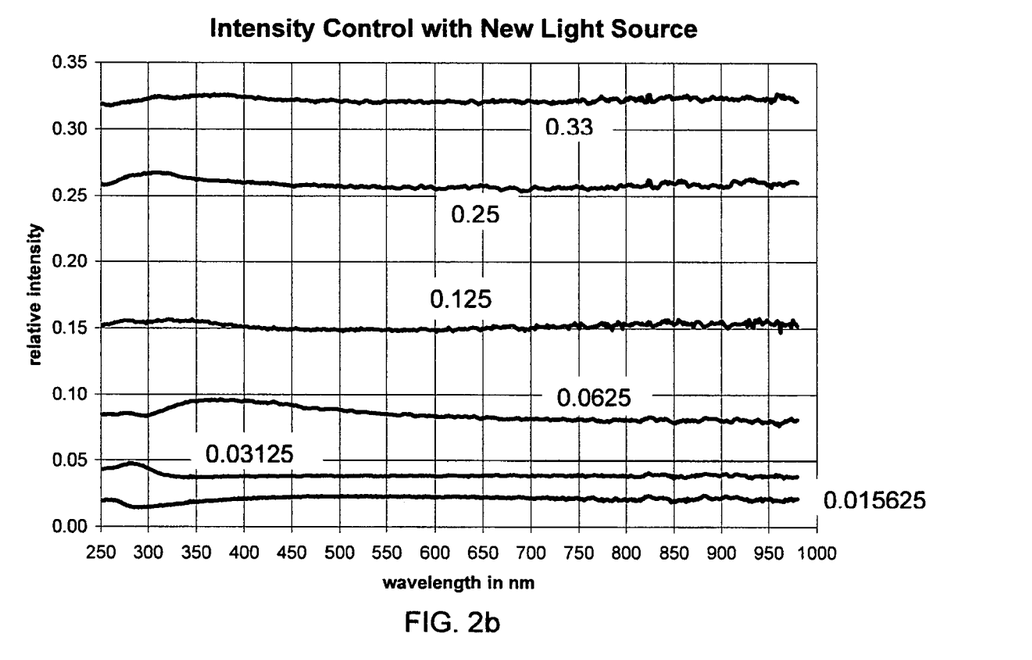
FIG. 2b shows the substantially achromatic attenuation vs. wavelength effect that passing the beam through different regions of the present invention attenuation system cause.

For insight, FIG. 2a shows a typical intensity vs. wavelength plot of a source of electromagnetic radiation from a, 150 Watt Xe arc lamp, which can be operated at 75 Watt to enable a long lifetime. FIG. 2b shows the substantially achromatic relative attenuation vs. wavelength effect that passing the beam through different regions of the present invention attenuation system cause.

Figure 3A:
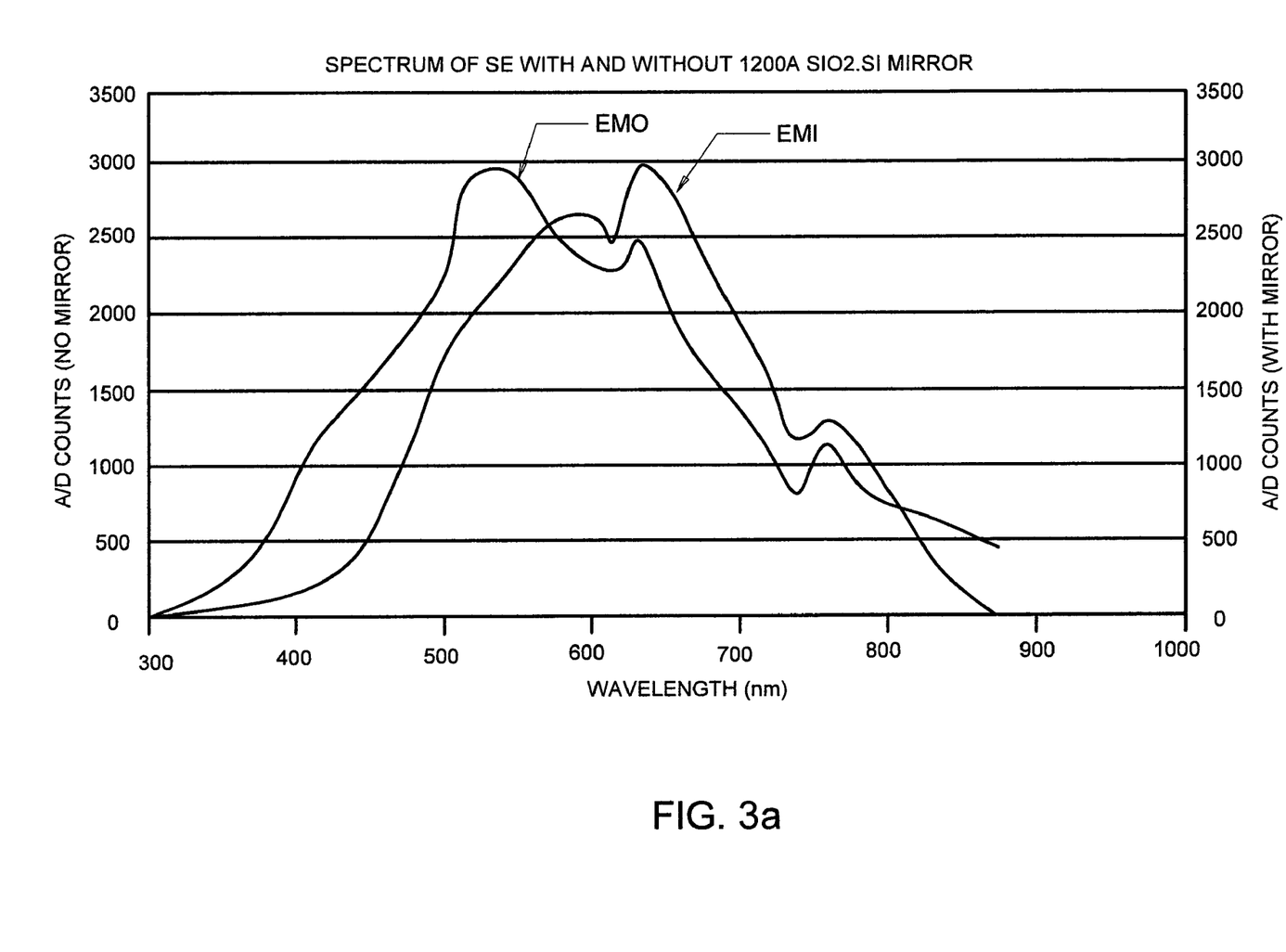
FIG. 3a shows the effect a reflective means, such as a substrate comprising SiO2 layer on Si, can have on relative attenuation of intensity of wavelengths in different wavelength ranges.
Figure 3B:
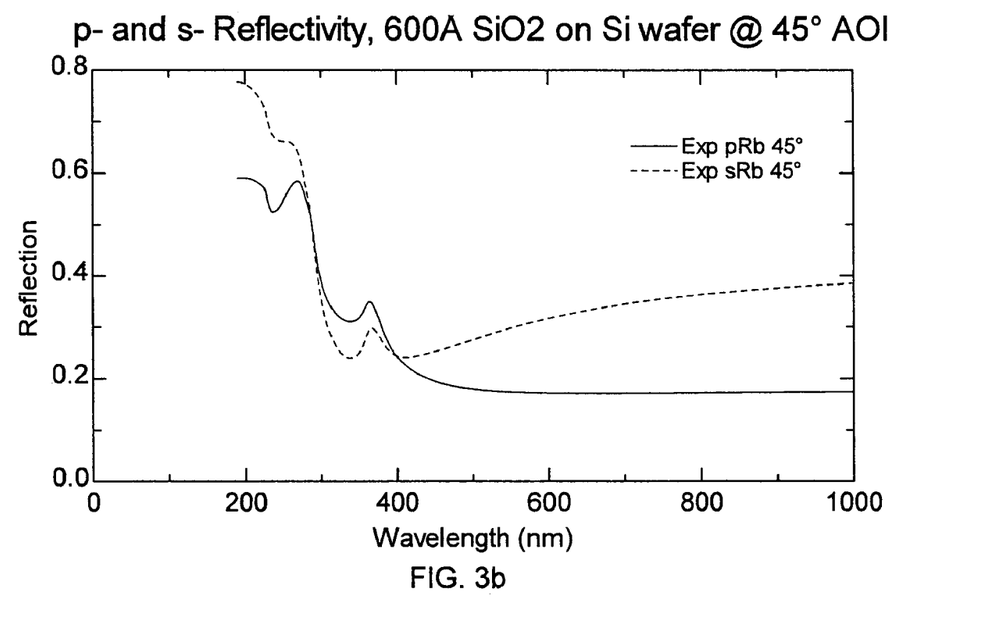
FIGS. 3b and 3c show the effect of a reflection from a reflection means as in FIG. 3a on "P" and "S" polarization component energy, (each relative to a standard of 1.0 as input), respectively.
Figure 3C:
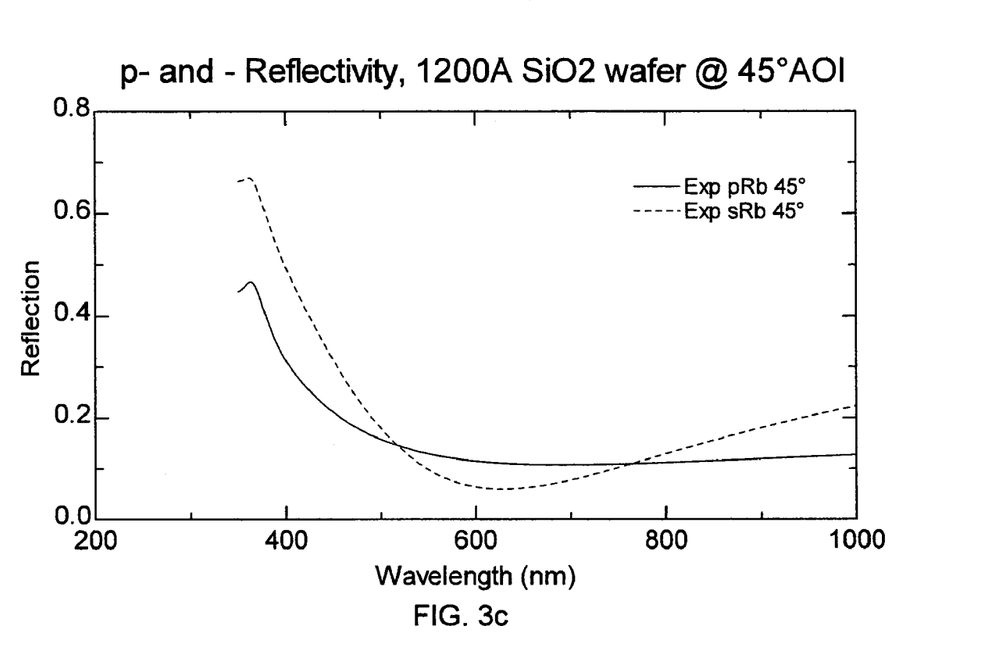

FIG. 3a shows the effect a reflective means, such as a substrate comprising SiO2 layer on Si, can have on relative attenuation of intensity of wavelengths in different wavelength ranges, where (EMI) is the input beam intensity and (EMO) is the Output beam Intensity. Note that the central region wavelengths are more attenuated that the wavelengths in the surrounding regions. FIGS. 3b and 3c show the amount of "P" and "S" polarization component energy, (each relative to a standard of 1.0 as input), respectively, which results from a reflection from a beam reflection as indicated in FIG. 3a. Note that FIG. 3b shows results where 600 Angstroms is present and FIG. 3b shows results where 1200 Angstroms is present on a Silicon Substrate.

Figure 4:
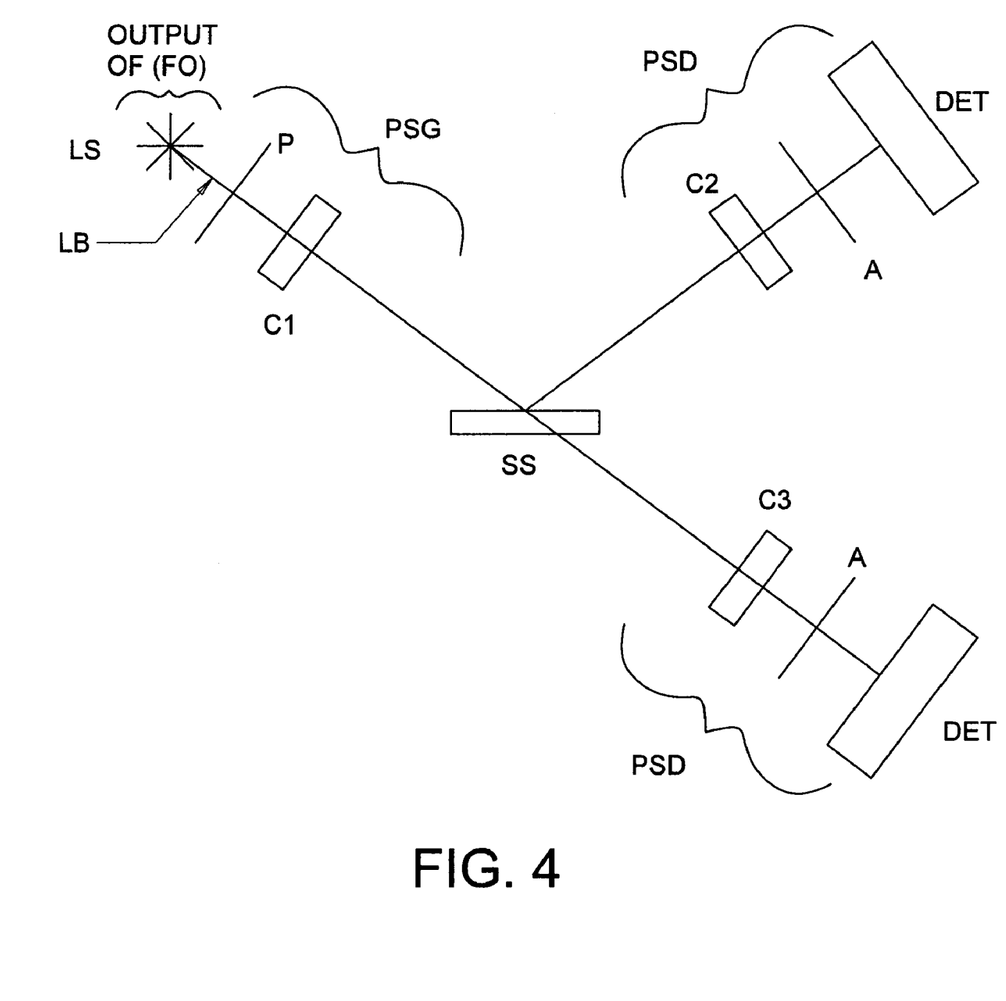
FIG. 4 shows an ellipsometer or polarimeter System.
Figure 5:
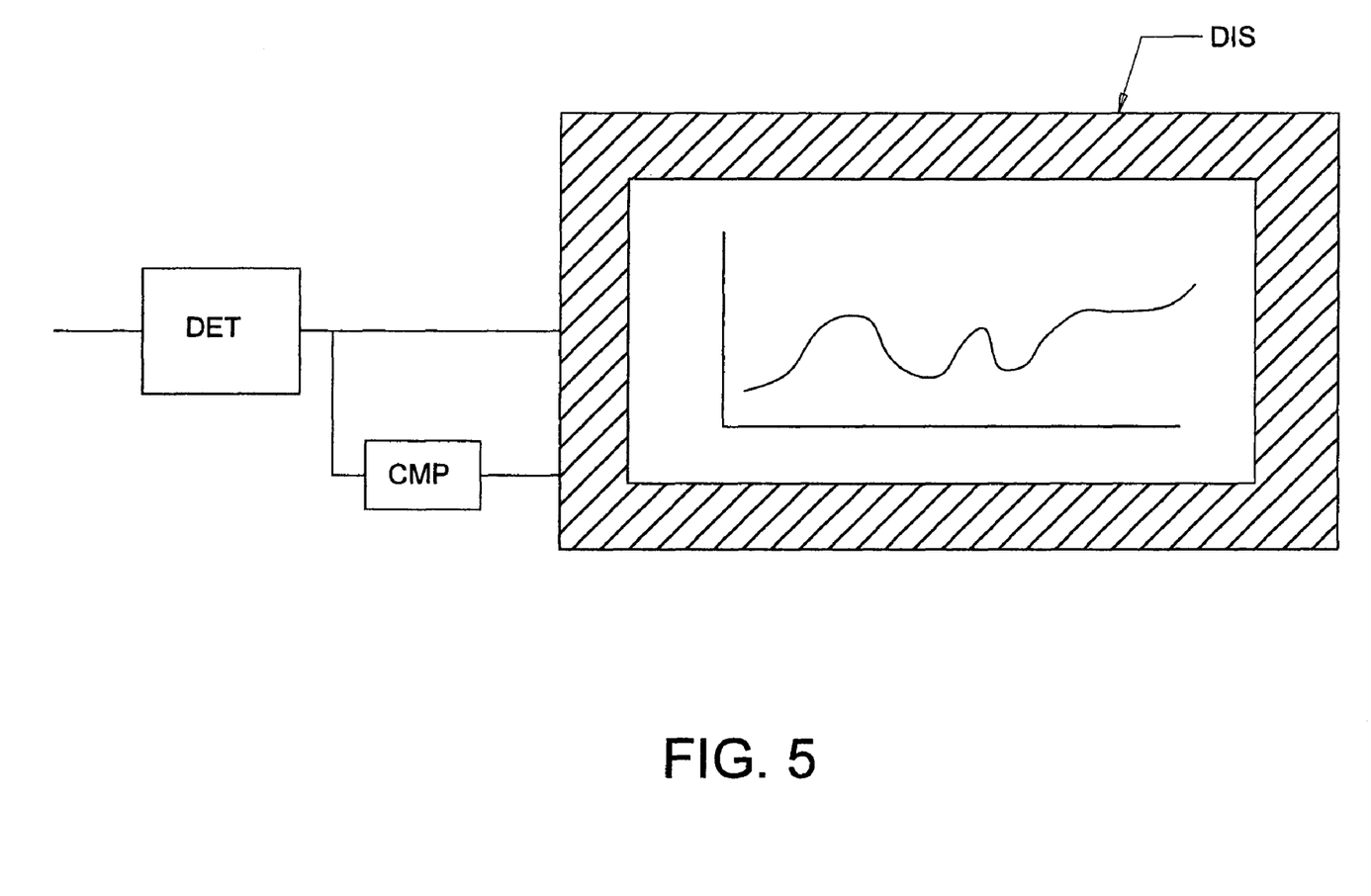
FIG. 5 shows that a Detector in FIG. 4 can provide output which is displayed directly, or analyzed by a Computer or the like (CMP) and Displayed.

As a very relevant use of the present invention system is in Ellipsometer and Polarimeter or the like Systems, FIG. 4 is provided to show said Ellipsometer and Polarimeter System generally comprise a Source of Electromagnetic Radiation (LS) which provides a beam (LB) which has a polarization state set by Polarizer (P) and Optional Compensator (C1) prior to interaction with a Sample (SS). Shown after the Sample (SS) are both Reflection and Transmission scenarios, each of comprise an Analyzer (A) and Optional Compensator (C2) (C3). Note that indications of Polarization State Generator (PSG) and Polarization State Detector (PSD) are shown. In the context of the present invention the Source of Electromagnetic Radiation (LS) is the system shown in FIG. 1. That is, the beam (LB) in FIG. 4 would emerge from the fiber optic (FO) in FIG. 1. It is noted that if the Polarizer (P) and Analyzer (A) and Compensators (C1) (C2) (C3) and designations of (PSG) and (PSD) are removed from FIG. 4, the result is a Spectrophotometer or Reflectometer or the like system. FIG. 5 shows that a Detector in FIG. 4 can provide output which is displayed directly, or analyzed by a Computer or the like (CMP) and Displayed. The signal from the Detector can also be used for other purposes, such a control of other systems.

Having hereby disclosed the subject matter of the present invention, it should be obvious that many modifications, substitutions, and variations of the present invention are possible in view of the teachings. It is therefore to be understood that the invention may be practiced other than as specifically described, and should be limited in its breadth and scope only by the Claims.

We claim:

1. A method of adjusting the intensity of a beam of electromagnetic radiation comprising the steps of:
   a) providing:
      a beam of electromagnetic radiation which has been collimated;
   and
      a combination of:
         a reflecting means, which demonstrates non-achromatic reflection characteristics in that different wavelengths are reflected with different intensity efficiencies therefrom, and
         an attenuation system which demonstrates substantially achromatic attenuation characteristics in that all wavelengths caused to pass therethrough are subjected to substantially equal relative intensity attenuations, said attenuation system comprising a circular wheel with regions thereof sequentially positioned circumferentially such that they can be variously placed in the beam by a rotation motion about the center of said wheel, said regions having different densities of quasi-uniformly distributed small holes or densities of electromagnetic radiation absorbing material and being characterized by selections from the group consisting of:
            R1 being 100% open;
            R2 being 1.56% open;
            R3 being 3.13% open;
            R4 being 6.25% open;
            R5 being 12.5% open;
            R6 being 25% open; and
            R7 being 50% open;
   b) causing said beam to reflect from said reflecting means and monitoring the resulting effect on intensity while applying a means for sequentially placing different regions of said attenuation system in the path of said beam of electromagnetic radiation to position a desired region thereof in the path of said beam, said beam being directed to enter a detector after passing through said means for sequentially placing different regions of an attenuation system in the path of said beam of electromagnetic radiation;

said method further comprising at least one selection from the group consisting of:
   storing at least some data provided by said detector in machine readable media;
   analyzing at least some of the data provided by said detector and storing at least some of the results of said analysis in machine readable media;
   displaying at least some data provided by said detector by electronic and/or non-electronic means;
   analyzing at least some of the data provided by said detector and displaying at least some of the results of said analysis by electronic and/or non-electronic means;
   causing at least some data provided by said detector to produce a signal which is applied to provide a concrete and tangible result;
   analyzing at least some of the data provided by said detector and causing at least some thereof to produce a signal which is applied to provide a concrete and tangible result.

2. A system selected from the group consisting of:
   an ellipsometer; and
   a polarimeter
system comprising:
   a polarization state generator (PSG) which comprises a source of electromagnetic radiation (LS) which provides a beam (LB) thereof, and a polarizer (P) prior to a sample (SS), and
   after said sample (SS) a reflection or transmission beam polarization state detector which comprises an analyzer (A), and a detector (DET);
wherein said source of electromagnetic radiation (LS) which provides a beam (LB) comprises:
   a source of a beam (EM) of electromagnetic radiation;
   a collimating lens (CL);
   a reflecting means (RM), which demonstrates non-achromatic reflection characteristics in that different wavelengths are reflected with different intensity efficiencies therefrom;
   a means for sequentially placing different regions of a substantially achromatic attenuation system (AS) in the path of a beam of electromagnetic radiation, said regions and having different densities of quasi-uniformly distributed small holes or densities of electromagnetic radiation absorbing material and being characterized by selections from the group consisting of:
      R1 being 100% open;
      R2 being 1.56% open;
      R3 being 3.13% open;
      R4 being 6.25% open;
      R5 being 12.5% open;
      R6 being 25% open; and
      R7 being 50% open;
   a focusing lens (FL); and
   a fiber optic (FO);
from which said fiber optic (FO), electromagnetic beam (LB) emerges;
such that in use said beam of electromagnetic radiation (LB) exiting said fiber optic is directed to pass through said polarization state generator (PSG), interact with said sample (SS), pass through said polarization state detector and is detected by said detector (DET).

3. A system as in claim 2, which further comprises at least one compensator in at least one selection from the group consisting of:

said polarization state generator; and
said polarization state detector.

4. A method of providing a desired amount of intensity attenuation to a beam of electromagnetic radiation comprising the steps of:
   a) providing a system for attenuating the intensity of a beam of electromagnetic radiation comprising:
   a source of a beam (EM) of electromagnetic radiation;
   a collimating lens (CL);
   a reflecting means (RM), which demonstrates non-achromatic reflection characteristics in that different wavelengths are reflected with different intensity efficiencies therefrom;
   a means for sequentially placing different regions of a attenuation system (AS) in the path of a beam of electromagnetic radiation;
   a focusing lens (FL);
   a fiber optic (FO); and
   a detector;
such that in use a beam (EM) of electromagnetic radiation is provided by the source thereof, is collimated by collimating lens (CL), redirected by reflecting means (RM), passes through a region of the attenuation system (AS), passes through the focusing lens (FL) and enters the end of a fiber optic (FO), interact with a sample (SS) and therevia entered into said detector;
   b) causing said source of a beam (EM) of electromagnetic radiation to provide a beam of electromagnetic radiation;
   c) while monitoring beam intensity, causing said means for sequentially placing different regions of an attenuation system (AS) in the path of said beam of electromagnetic radiation to position a desired region thereof in the path of said beam;
said method further comprising at least one selection from the group consisting of:
   storing at least some data provided by said detector in machine readable media;
   analyzing at least some of the data provided by said detector and storing at least some of the results of said analysis in machine readable media;
   displaying at least some data provided by said detector by electronic and/or non-electronic means;
   analyzing at least some of the data provided by said detector and displaying at least some of the results of said analysis by electronic and/or non-electronic means;
   causing at least some data provided by said detector to produce a signal which is applied to provide a concrete and tangible result;
   analyzing at least some of the data provided by said detector and causing at least some thereof to produce a signal which is applied to provide a concrete and tangible result.

5. A method of adjusting the intensity of a beam of electromagnetic radiation comprising the steps of:
   a) providing a selection from the group consisting of:
      an ellipsometer; and
      a polarimeter; comprising:
         a polarization state generator (PSG) which comprises a source of electromagnetic radiation (LS) which provides a beam (LB), and a polarizer (P) prior to a sample (SS), and
         after said sample (SS) a reflection or transmission beam polarization state detector which comprises an analyzer (A), and a detector (DET);
   wherein said source of electromagnetic radiation (LS) which provides a beam (LB) comprises:
      a source of a beam (EM) of electromagnetic radiation;
      a collimating lens (CL);
      a reflecting means (RH);
      a means for sequentially placing different regions of an attenuation system (AS) in the path of a beam of electromagnetic radiation;
      a focusing lens (FL); and
      a fiber optic (FO);
   such that in use a beam (LB) of electromagnetic radiation is provided by the source thereof, is collimated by collimating lens (CL), is redirected by reflecting means (RM), passes through a region of the attenuation system (AS), passes through the focusing leans (FL) and enters an end of said fiber optic (FO), then exits said fiber optic, interacts with said sample (SS) and enters into said detector;
   b) monitoring the output of the detector (DET) of the ellipsometer or polarimeter system while sequentially placing different regions of the attenuation system (AS) in the path of a beam of electromagnetic radiation;
said method further comprising at least one selection from the group consisting of:
   storing at least some data provided by said detector in machine readable media;
   analyzing at least some of the data provided by said detector and storing at least some of the results of said analysis in machine readable media;
   displaying at least some data provided by said detector by electronic and/or non-electronic means;
   analyzing at least some of the data provided by said detector and displaying at least some of the results of said analysis by electronic and/or non-electronic means;
   causing at least some data provided by said detector to produce a signal which is applied to provide a concrete and tangible result;
   analyzing at least some of the data provided by said detector and causing at least some thereof to produce a signal which is applied to provide a concrete and tangible result.

6. A system as in claim 5, which further comprises at providing at least one compensator in at least one selection from the group consisting of:
   said polarization state generator; and
   said polarization state detector.

7. A method as in claim 5, in which the step of providing the system involves providing a reflecting means (RM) which demonstrates non-achromatic characteristics in that different wavelengths are reflected with different intensity efficiencies therefrom.

8. A Spectrophotometer or Reflectometer comprising a source of a beam of electromagnetic radiation, a sample and a detector of electromagnetic radiation after interaction with said sample, comprising as the source of said beam:
   a system for attenuating the intensity of a beam of electromagnetic radiation comprising:
      a collimating lens (CL);
      a reflecting means (RM), which demonstrates non-achromatic reflection characteristics in that different wavelengths are reflected with different intensity efficiencies therefrom;
      a reflecting means (RM);
      a means for sequentially placing different regions of a substantially achromatic attenuation system (AS) in the path of a beam of electromagnetic radiation, said regions having different densities of quasi uniformly distributed small holes or densities of electromagnetic radiation absorbing material and being characterized by selections form the group consisting of:

R1 being 100% open;
R2 being 1.56% open;
R3 being 3.13% open;
R4 being 6.25% open;
R5 being 12.5% open;
R6 being 25% open; and
R7 being 50% open;
a focusing lens (FL); and
a fiber optic (FO);

such that in use a beam (EM) of electromagnetic radiation is provided by the source thereof, is collimated by collimating lens (CL), redirected by reflecting means (RM), passes through a region of the attenuation system (AS), passes through the focusing lens (FL) and enters the end of a fiber optic (FO).

9. A method of adjusting the intensity of a beam of electromagnetic radiation comprising the steps of:
 a) providing a selection from the group consisting of:
  a spectrophotometer; and
  a reflectometer;
comprising a source (LS) of a beam (LB) of electromagnetic radiation, a sample (SS) and a detector (DET) of electromagnetic radiation after said sample (SS),
wherein said source of said beam comprises:
 source of a beam (EM) of electromagnetic radiation;
 a collimating lens (CL);
 a reflecting means (RM);
 a means for sequentially placing different regions of an attenuation system (AS) in the path of a beam of electromagnetic radiation;
 a focusing lens (FL); and
 a fiber optic (FO);
such that in use a beam (EM) of electromagnetic radiation is provided by the source thereof, is collimated by collimating lens (CL), is redirected by reflecting means (RM), passes through a region of the attenuation system (AS), passes through the focusing lens (FL) and enters an end of said fiber optic (FO), then exits said fiber optic, interacts with said sample (SS) and enters into said detector (DET);
 b) monitoring the output of the detector (DET) of the spectrophotometer or reflectometer system while sequentially placing different regions of the attenuation system (AS) in the path of a beam of electromagnetic radiation;
said method further comprising at least one selection from the group consisting of:
 storing at least some data provided by said detector in machine readable media;
 analyzing at least some of the data provided by said detector and storing at least some of the results of said analysis in machine readable media;
 displaying at least some data provided by said detector by electronic and/or non-electronic means;
 analyzing at least some of the data provided by said detector and displaying at least some of the results of said analysis by electronic and/or non-electronic means;
 causing at least some data provided by said detector to produce a signal which is applied to provide a concrete and tangible result;
 analyzing at least some of the data provided by said detector and causing at least some thereof to produce a signal which is applied to provide a concrete and tangible result.

10. A method as in claim 9, in which the step of providing the system involves providing a reflecting means (RM) which demonstrates non-achromatic characteristics in that different wavelengths are reflected with different intensity efficiencies therefrom.

* * * * *